United States Patent [19]

Sarfarazi

[11] Patent Number: 5,476,512
[45] Date of Patent: Dec. 19, 1995

[54] ANTERIOR CAPSULAR FIXATING LENS FOR POSTERIOR CAPSULAR RUPTURES

[76] Inventor: Faezeh Sarfarazi, 25 Wiswall Rd., Newton Center, Mass. 02159

[21] Appl. No.: 795,004

[22] Filed: Nov. 18, 1991

[51] Int. Cl.⁶ .................................................. A61F 2/16
[52] U.S. Cl. ........................................................ 623/6
[58] Field of Search ..................................... 623/6

[56] References Cited

U.S. PATENT DOCUMENTS

| | | | |
|---|---|---|---|
| 3,906,551 | 9/1975 | Otter | 623/6 |
| 3,925,825 | 12/1975 | Richards et al. | 623/6 |
| 3,971,073 | 7/1976 | Richards et al. | 623/6 |
| 4,079,470 | 3/1978 | Deeg et al. | 623/6 |
| 4,124,905 | 11/1978 | Clark | 623/6 |
| 4,172,297 | 10/1979 | Schlegel | 623/6 |
| 4,177,526 | 12/1979 | Kuppinger | 623/6 |
| 4,206,518 | 6/1980 | Jardon et al. | 623/6 |
| 4,240,163 | 12/1980 | Galin | 623/6 |
| 4,485,598 | 12/1984 | Gimbel | 623/6 |
| 4,605,409 | 8/1986 | Kelman | 623/6 |
| 4,750,904 | 6/1988 | Price, Jr. | 623/6 |
| 4,946,469 | 8/1990 | Sarafarazi | 623/6 |
| 5,171,320 | 12/1992 | Nishi | 623/6 |

Primary Examiner—Mary Beth O. Jones
Attorney, Agent, or Firm—Ellen C. Childress

[57] ABSTRACT

An intraocular lens assembly is presented for implantation into the posterior chamber after rupture of the posterior capsule during extracapsular extraction, using the capsulorhexis technique, of the natural lens assembly. The lens assembly has anterior ciliary sulcus haptics and posterior capsular bag haptics which straddle the remaining anterior capsule.

2 Claims, 4 Drawing Sheets

ANTERIOR CAPSULAR FIXATING LENS FOR POSTERIOR CAPSULAR RUPTURES

FIELD OF THE INVENTION

This invention relates to intraocular lenses for implanting in the posterior chamber of the eye when the posterior capsule has been ruptured.

BACKGROUND OF THE INVENTION

Cataract extraction is the most common ophthalmic surgical procedure performed in the United States. Extracapsular cataract extraction involves cutting a portion of the anterior capsule (anterior capsulorhexis) followed by removal of the nucleus. Alternatively, a probe may be inserted through the anterior capsule and ultrasonically vibrated, transforming lens material into an emulsion is then irrigated and aspirated from the capsular bag (phacoemulsification). After removal of the natural lens, images no longer focus on the retina and a replacement lens must be provided for clear vision. Replacement lenses can be glasses, contact lenses or intraocular lenses. Of these, intraocular lenses give the greatest convenience and undistorted vision. In ten percent or greater of extracapsular extractions, the posterior capsule is ruptured during aspiration of the cortex, making it impossible to use regular posterior lens implantation in the bag. Prior to the invention, anterior chamber intraocular lenses have been used as standbys since commercially available capsular lenses would enlarge the tear. Such anterior chamber lenses can cause complications such as damage to the vascularly rich iris of the eye.

U.S. Pat. No. 4,750,904, incorporated herein by reference, explains some complications arising from anterior chamber implants. This patent discloses a posterior chamber lens sutured directly to the iris for use after an intraocular lens extraction has left no capsular platform to hold a lens.

The present invention is directed toward the use of the ciliary sulcus and the anterior capsular membrane to retain and support a lens in the natural position.

BRIEF SUMMARY OF THE INVENTION

The present invention provides lenses having optics supported by haptics which engage the sulcus and straddle the anterior capsule through a capsulorhexis if the posterior capsule is damaged. A variety of embodiments are presented.

DESCRIPTION OF THE PREFERRED EMBODIMENTS

Figure 1:
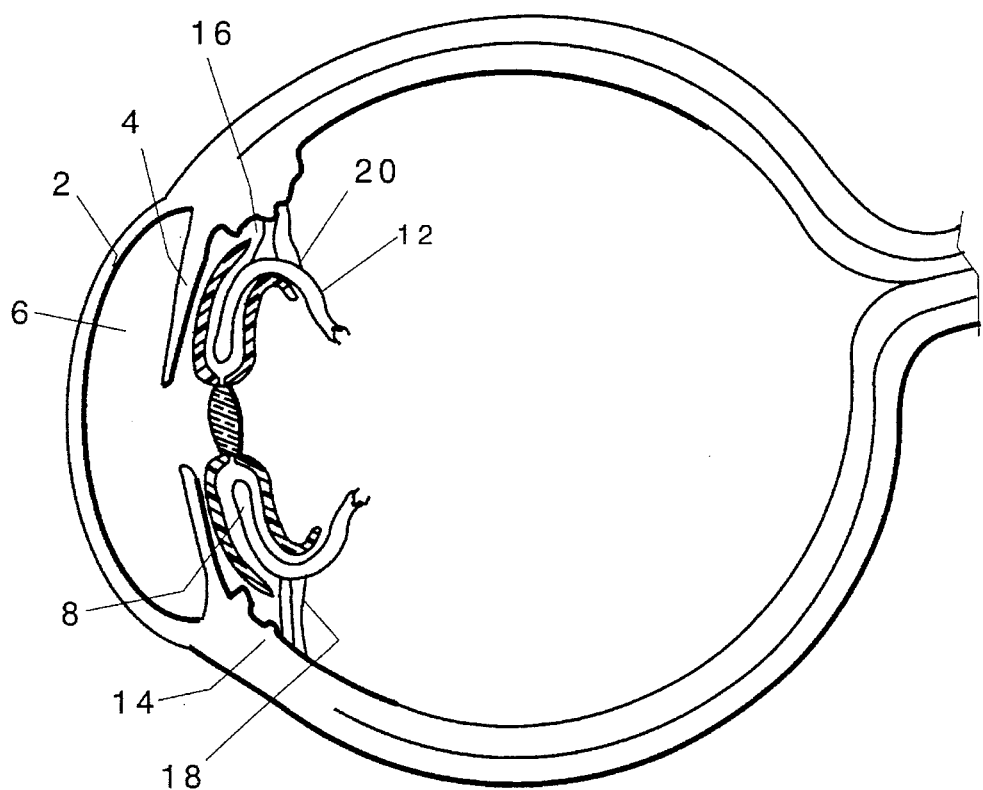
FIG. 1 is a cross sectional view of an eye having a posterior capsular tear showing the placement of an anterior capsular fixating lens according to the invention.
Figure 2:
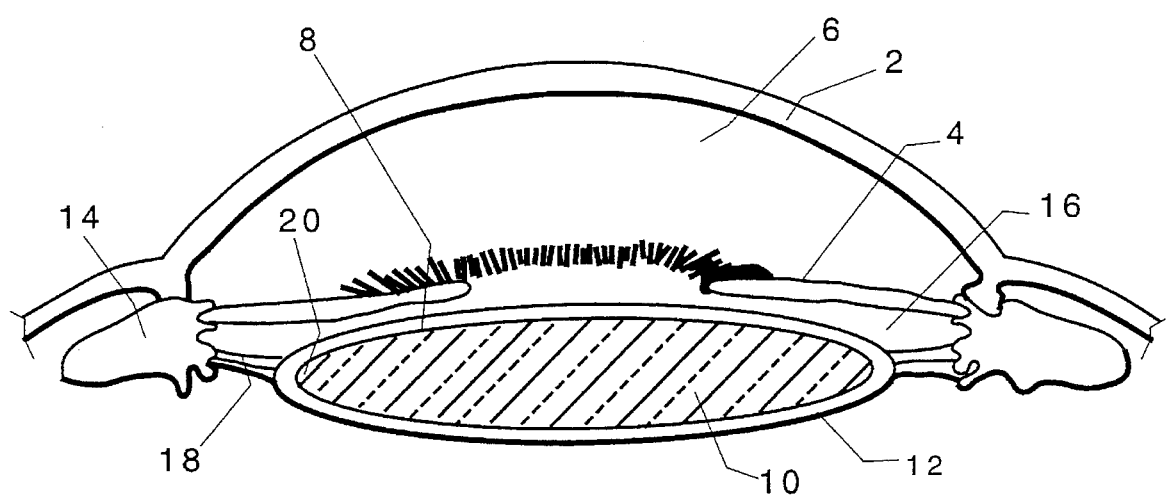
FIG. 2 is a schematic cross sectional view of the frontal portion of an eye.

FIG. 2 shows a partial section of an eye. The cornea 2 is separated from iris 4 by the aqueous humor in the anterior chamber 6. Behind iris 4 lies the anterior capsule 8, lens 10 and the posterior capsule 12. Beneath the posterior capsule is the vitreous humor. A furrow is formed between the iris 4 and the ciliary muscle 14 called the ciliary sulcus 16. A furrow is also formed in the capsular bag where the zonules 18 are attached. This will be referred to as the bag sulcus 20. During extracapsular extraction the natural lens 10 is removed.

Figure 3:
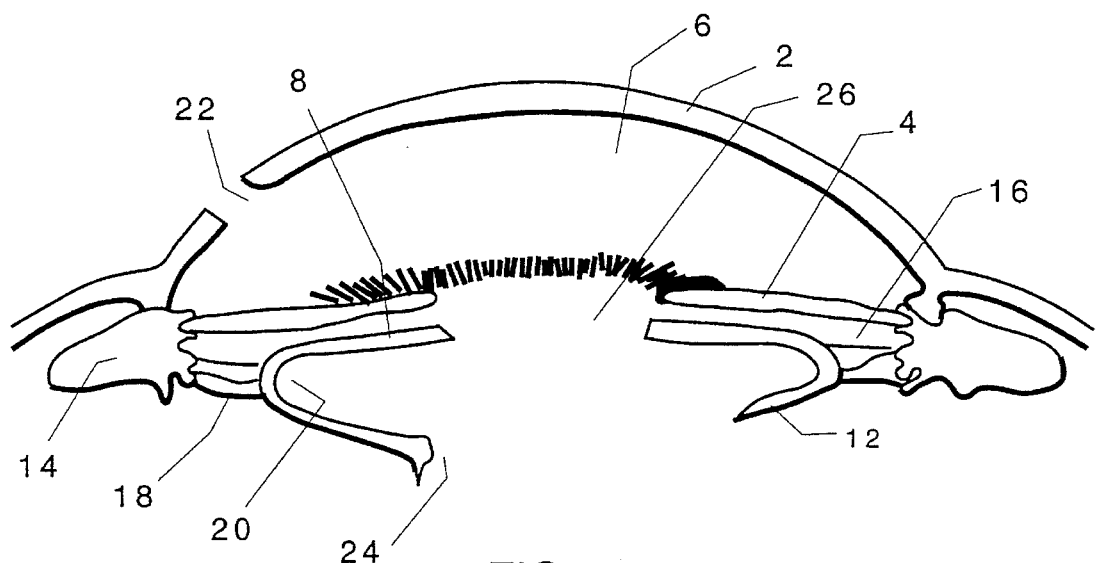
FIG. 3 is a cross sectional view showing a capsulorhexis opening and a torn posterior capsule.

FIG. 3 shows a perspective view an eye after extracapsular extraction. An incision 22 at the outer edge of the cornea 2 has allowed for the central portion of the anterior capsule 8 (capsulorhexis) to be removed 26. Due to surgical complications the posterior capsule 12 has developed a tear 24.

Figure 4:
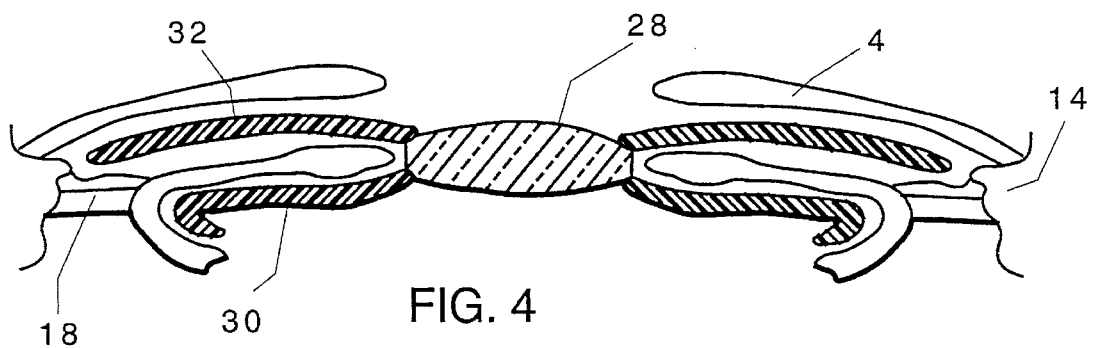
FIG. 4 is a cross sectional view showing placement of an intraocular lens of the invention.

FIG. 4 shows a first embodiment of the invention and its placement through the anterior capsulorhexis. This is possible due to the elastic nature of the anterior capsular wall. Optic 28 has attached two haptic assemblies: shorter capsular haptics 30 and longer ciliary sulcus haptics 32. Together, these haptic assemblies for a sandwich around the anterior capsular wall to support the optic 28. The capsular haptic has a spring-like action biased toward the ciliary sulcus haptic.

Figure 5:
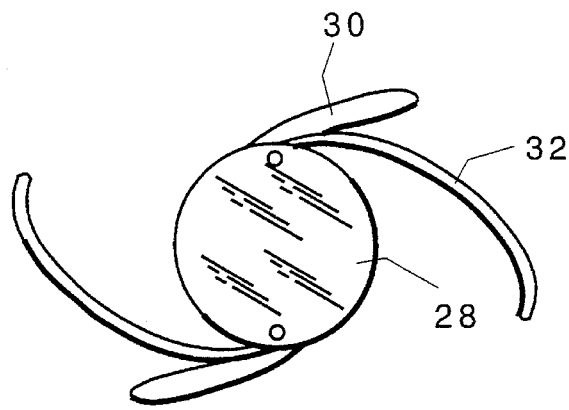
FIG. 5 is a top view of the lens of FIG. 3.

The embodiment shown in FIG. 5 has an optic 28 having J or C shape projecting (linear) haptics 32 to engage the ciliary sulcus and straight or C shape capsular haptics 30.

Figure 6:
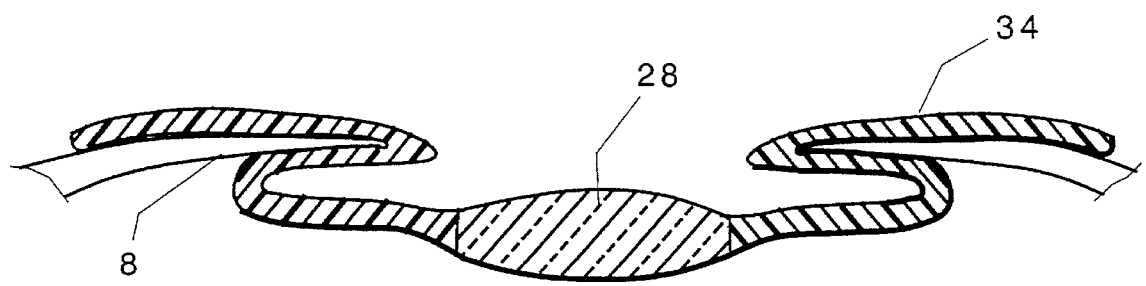
FIG. 6 is a side view of a second embodiment having a combined ciliary sulcus and capsular bag haptic.

The embodiment shown in FIG. 6 has combined ciliary sulcus and capsular haptic sections 34. The capsular sulcus segment loops back around to become the ciliary sulcus haptic segment.

Figure 7:
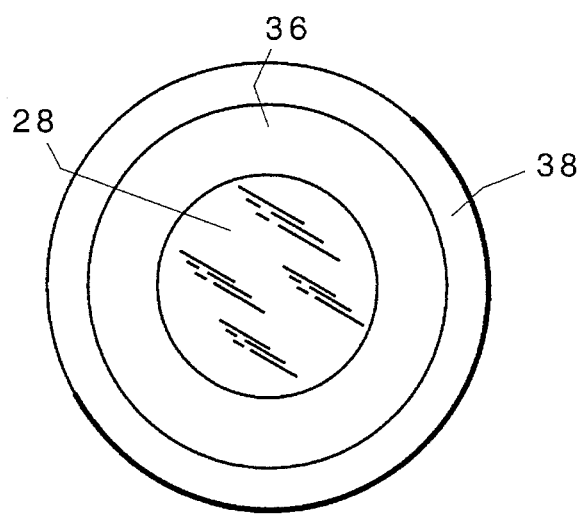
FIG. 7 is a top view of a third embodiment of the invention having flexible annular haptics.
Figure 8:
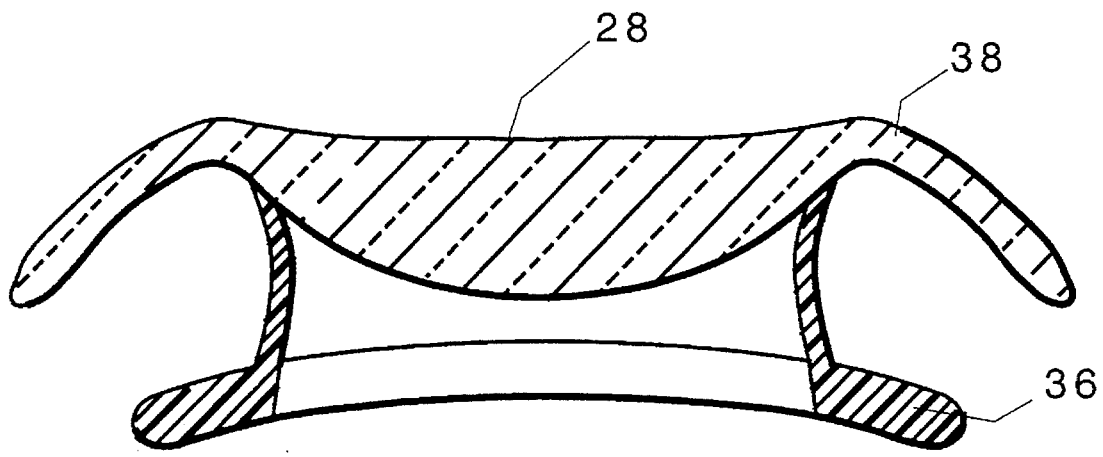
FIG. 8 is a side view of the lens assembly of FIG. 6 having a concavo-convex lens.

FIGS. 7 and 8 show an optic 28 having a soft, flexible annular haptics such as described in U.S. Pat. No. 4,946,469, incorporated herein by reference. The smaller annular haptic is the capsular haptic 36 which has an central aperture. The larger annular haptic is the ciliary sulcus haptic 38. Although the optic shown is concavo-convex, the optic may be made with any combination of concave, flat or convex surfaces to accommodate individual needs.

Figure 9:
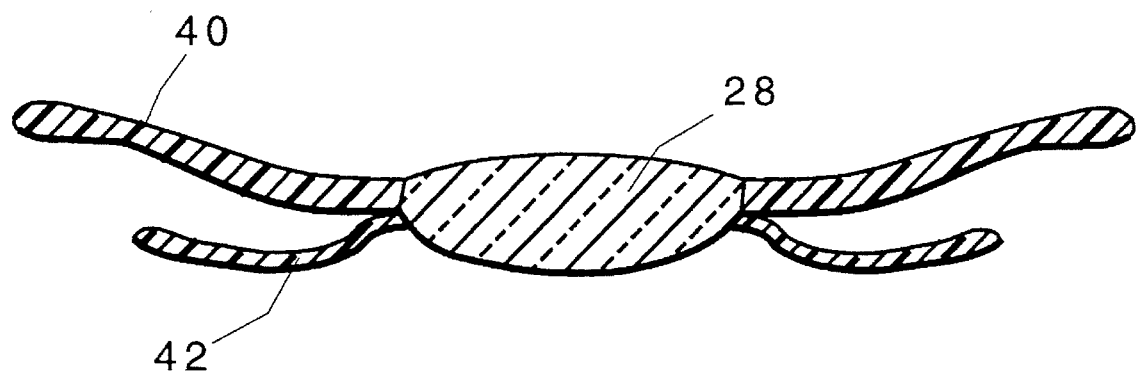
FIG. 9 is a side view of a fourth embodiment having a combination of annular and linear type haptics.

FIG. 9 shows still another embodiment of the invention. Optic 28 is provided with an annular ciliary sulcus haptic 40 and a linear capsular haptic 42.

Suitable materials for the optic portion of the lens assembly are biocompatible, transparent materials such as PMMA (polymethyl methacrylate), HEMA (hydroxyethyl methacrylate), polysulfones, polycarbonates, or a silicone polymers (polydimethyl siloxanes).

Preferred materials for haptic portions are PMMA and polyolefins such as polypropylene. The equatorial diameter of the optic portion is about 5 mm. and has a thickness between 1 and 3 mm., preferably 2.4 mm. The diameter spanned by the ciliary sulcus haptic is between 10 and 13 mm., preferably 11.5 mm. The diameter spanned by the bag haptic is between 8 and 10.5 mm., preferably 9.0 mm. Any linear or annular type haptic assemblies found in the literature may be combined to support the optic through the anterior capsulorhexis.

The method of use is as follows: After opening the cornea and performing a capsulorhexis the nucleus is extracted and remaining lens material aspirated. If a capsular rupture occurs, the anterior fixating lens is grasped with a forceps and inserted first through the pupil. The lens is then tilted slightly so that one set of capsular and ciliary sulcus haptics are placed over the remaining anterior capsule. Half of the sulcus haptic is pushed Gently into the ciliary sulcus. The lens is then pushed forward and downward Gently to slip the capsular haptic into the bag and the remainder of the ciliary sulcus haptic into place. With one set of haptics inserted, the uninserted haptics are Guided into place.

Lens assemblies in accordance with the invention, provide opthamalogical surgeons with a superior alternative to present anterior chamber lens when a ruptured posterior capsule occurs during extracapsular extraction of a natural lens.

What is claimed is:

1. An intraocular lens assembly for placement in the posterior chamber of an eye from which the natural lens has been removed by an anterior capsulorhexis comprising:

a central optical portion formed of a transparent refractive material; and at least one haptic portion extending from said central optical portion, said at least one haptic portion having a segment of a dimension sufficiently large enough to engage a ciliary sulcus and a second segment having a lesser overall dimension for engaging a capsular bag such that said at least one haptic portion supports said optical portion.

wherein the most anterior point on said at least one haptic portion is anterior to the most anterior point on said central optical portion.

2. An intraocular lens assembly for placement in the posterior chamber of an eye from which the natural lens has been removed by an anterior capsulorhexis comprising:

a central optical portion formed of a transparent refractive material; and means for straddling the remaining anterior capsular wall, said means comprising a first segment for engaging the ciliary sulcus and a second segment for engaging the remaining anterior capsular wall; said means extending from and supporting said central optical portion.

wherein the most anterior point on said straddling means is anterior to the most anterior point on said central optical portion.

* * * * *